United States Patent
Schönharting et al.

(12)

(10) Patent No.: US 6,432,968 B1
(45) Date of Patent: Aug. 13, 2002

(54) COMBINATION PREPARATION, CONTAINING CYCLOSPORIN A OR FK506 OR RAPAMYCIN AND A XANTHINE DERIVATIVE

(75) Inventors: Martin Schönharting, Taunusstein; Ulrich Gebert, Glashütten, both of (DE); Mark Waer, Heverlee (BE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/437,829

(22) Filed: Nov. 10, 1999

Related U.S. Application Data

(63) Continuation of application No. 08/817,218, filed as application No. PCT/EP95/03126 on Aug. 7, 1995, now Pat. No. 6,046,328.

(30) Foreign Application Priority Data

Aug. 25, 1994 (DE) .......................................... 44 30 127

(51) Int. Cl.[7] .......................... A61K 31/52; A61K 31/44; A61K 38/00
(52) U.S. Cl. .......................... 514/264; 514/291; 514/11
(58) Field of Search ................................. 514/264, 291, 514/11

(56) References Cited

FOREIGN PATENT DOCUMENTS

| | | |
|---|---|---|
| EP | 0 490 181 | 6/1991 |
| EP | 0 493 682 | 7/1992 |
| WO | 92/07566 | 5/1992 |
| WO | 93/17684 | 9/1993 |

OTHER PUBLICATIONS

Merck Index, 10th ed, Windholz et al Ed. Merck, Dohm & Sharp, Rahway, NJ, No. 2748, Jan. 1985.*
Kino et al, 107CA:211596, Jan. 1987.*
Kino et al, 107CA:228689, Jan. 1987.*
Sawada et al, 107CA;228682, Jan. 1985.*
Burserud, Oeystein, The additive effect of certain drugs on the cyclosportin A inhibition of human T–cell proliferation, APMIS 98(12) 170–6.

* cited by examiner

*Primary Examiner*—Russell Travers
(74) *Attorney, Agent, or Firm*—Heller Ehrman White & McAuliffe LLP

(57) ABSTRACT

Xanthines of the formula I (I)

are useful in producing a superadditive increase in immunosuppressive action when combined with immunosuppressive compounds such as CysA or FK506.

21 Claims, No Drawings

COMBINATION PREPARATION, CONTAINING CYCLOSPORIN A OR FK506 OR RAPAMYCIN AND A XANTHINE DERIVATIVE

This application is a continuation of application Ser. No. 08/817,218, now U.S. Pat. No. 6,046,328, filed Apr. 3, 1997 which is a 371 of PCT/EP95/03126 filed Aug. 7, 1995, claiming priority from German Patent 44 30 127 filed Aug. 25, 1994.

Cyclosporin A (CysA) is a cyclic undecapeptide which is obtained from a fungus (CAS No.59865-13-3; U.S. Pat. No. 3,737,433). Its immunosuppressive effect has been known since 1972, but nevertheless it still took about 10 years until CysA found its way into the treatment of the acute rejection reaction of transplants (Borel J. F.: Cyclosporine. In: Dale M., Foreman J. C., Fan T. P. D. (eds.): Textbook of Immunology (3rd ed.). Blackwell Scient. Publ. Oxford 1994 pp 320–329). Today, as a result of its outstanding properties, CysA can no longer be overlooked in immunosuppression, even if its use is accompanied by a number of sometimes serious side effects.

The immunosuppressive action of CysA is very selective and concentrates on T-cell-dependent mechanisms. CysA inhibits the proliferation of T-lymphocytes, which normally respond to a proliferative stimulus (produced e.g. by antigen or nitogen) with cell replication and cell differentiation but also the release of lymphokines (e.g. various interleukins such as IL-2, IL-3 and IL-4, but also γ-interferon) and in this way start the cellular immune response. T-cell-independant B cell-dependent mechanisms (e.g. the humoral immune response via certain antibodies) cannot be inhibited, however, under the therapeutically achievable CysA concentrations. The immuno-suppression produced by CysA is completely reversible after removing or washing out the substance (Thomson A. W. (ed.): Cyclosporin: Mode of Action and Clinical Applications. Kluwer Acad. Publ. Dordrecht 1989), which points to the fact that it is not a general lymphocytotoxic reaction which we are dealing with here, instead the release of IL-2 by T-helper cells primarily appears to be inhibited, which brings about a blockade of secondary immunological reactions. In this case the expression of the IL-2 gene represents the biochemical response of the T-helper cell to an immunological stimulus, which is fed from the cell membrane into the nucleus in the course of a "signal chain". Although the individual biochemical chain constituents and their sequence have not yet been elucidated in detail, the activation and translocation of a cytosolic "nuclear factor" (NF-AT=nuclear factor of activated T cells) can be assumed as an important step which then causes the transcription of the IL-2 gene in the nucleus. This activation of NF-AT which is controlled by the $Ca^{2+}$/calmodulin/calcineurin system is inhibited by CysA, which joins intracellularly with a protein called "cyclophilino" to give a complex (Handschumacher R. E. et al.: Science 226 (1984), 544–546), with the result that despite the presence of an immunological stimulus no IL-2 is formed which, however, is of crucial importance for the further course of the cellular immune response (inter alia for the formation of cytotoxic T-cells).

This immunosuppressive action appears CysA to be suitable not only for allogeneic transplantations, but also for autoimmune disorders of different manifestation. In fact, numerous respective therapeutic attempts have been undertaken, from rheumatoid arthritis through psoriasis up to juvenile diabetes (Schindler R. (ed.): Cyclosporin in Autoimmune Diseases. Springer Verlag Berlin 1985; Thomson A. W. et al.: Br. Med. J. 302 (1991), 4–5). Despite various successful results, however, CysA has not been able to establish itself as the drug of choice in these indications, the reason for this being exclusively to be sought in the toxicity of this substance. In the first place, its marked nephrotoxicity which in some cases is irreversible has to be mentioned here, but also other phenomena such as high blood pressure, nausea, diarrhoea, tremor, tingling or gingival hypertrophy (Palestine A. R. et al.; Am. J. Med. 77 (1984), 652–656) represent complications to be taken seriously, which usually cannot be avoided even with systematic checking of the serum level. At the same time—as with any effective immunosuppression—opportunistic infections additionally have to be considered (Dawson T. et al.: J. Rheumattl. 19 (1992), 997), so that by critical benefit-risk assessment an otherwise advantageous CysA medication in many cases has to be sacrificed.

Xanthines have already been taken by people for many hundreds of years in the form of aqueous extracts, and the stimulating as well as diuretic properties of tea or coffee are generally known. About 70 years ago, theophylline was then introduced into medicine as a pure substance for the treatment of pulmonary complaints (e.g. asthma attack), followed 50 years later by pentoxifylline (POF), which is employed for the treatment of peripheral and cerebral circulatory disorders (Ward A. et al.: Drugs 34 (1987), 50–97). The latter xanthine derivative, which clearly differs from theophylline due to its extensive lack of central and cardiac effects, in the following was subject of in-depth investigations on its mechanism of action, in the course of which also effects on the immune system have been detected. Thus, for example, it was already found at the start of the '80s that POF significantly prolonged the survival rate of heart and kidney transplants in the rat model, although these findings, at that time, have primarily been attributed to improved circulatory phenomena (Kostakis A. J. et al.: IRCS 8 (1980), 15; Kostakis A. J. et al.: IRCS Med. Sci. 10 (1982), 77–78). Only later was it recognized that POF—together with other representatives of the xanthine family—interacts with the immunologically important cytokine network. This is not only true for tumor necrosis factor (TNF), which plays a central role in a number of very different disorders and whose formation is inhibited on the transcriptional level by POF (Strieter R. M. et al.: Biochem. Biophys. Res. Commun. 155 (1988), 1230–1236), but also for other cytokines such as IL-2 or IFNγ (Rieneck K. et al.: Immunol. Lett. 37 (1993), 131–138; Thanhäuser A. et al.: Immunology 80 (1993), 151–156; Tilg H. et al.: Transplantation 56 (1993), 196–201). Since, in addition antiproliferative effects of POF also became known in the meantime (Singer J. W. et al.: Bone Marrow Transplant. 10 (1992), 19–25), it is not astonishing that today certain immunomodulatory properties are ascribed to POF, which have already given rise to speculations about an extension of its present applications (Zabel P. et al.: Immun. Infect. Dis. 3 (1993), 175–180).

As far as the mechanism of action of xanthines is concerned, the cAMP system may play a predominant role. cAMP (cyclic 3',5'-adenosine monophosphate) is a "second messenger" and able to control the activity state of the cell: the higher the intracellular cAMP level, the less activated the cell. The height of the cAMP level may generally be affected by two different mechanisms: increase in formation by adenylate cyclase (AC) or inhibition of degradation by phosphodi-esterase(s) (PDE). Xanthines from the POF series are prone to both of these possibilities, i.e. directly via inhibition of PDE and indirectly via stimulation of the release of prostaglandins, which themselves stimulate AC's.

Actually, the increase in intracellular cAMP level due to xanthine action—with all its consequences—is not restricted to T-lymphocytes, however, but is also found in other immunocompetent cells such as monocytes or granulocytes, which in the former leads to the inhibition of TNF synthesis (Strieter R. M. et al.: Diochem, Biophys. Res. Commun. 155 (1988), 1230–1236) but in the latter suppresses the "metabolic burst" (=oxygen free radical formation and release of lytic enzymes from the granules for bacterial infection defence (Hammerschmidt D. E. et al.: J. Lab. Clin. Med. 112 (1988), 254–263)), both reactions of which—intravasally induced—being able to cause massive complications in the microcirculation. This mechanism, which in the various representatives of the xanthine family may differ markedly (Semmler J. et al.: Immunology 78 (1993), 520–525), indeed leads to very selective interventions in the cytokine network (the formation of IL-1, for example, is nearly not affected at all (Tannenbaum C. S. et al.: J. Immunol. 142 (1989), 1274–1280; Endres S. et al. Immunology 72 (1991), 56–60), thus reducing the vascular and the immunological modes of action of xanthines to a common biochemical basis (Schbnharting M. M.: In: Kark B., Werner H. (eds.): Herz- und Kreislaufer-krankungen im Alter. Steinkopff-Verlag Darmstadt 1990, pp 3–13).

Apart from its general potential to increase cAMP levels both directly and indirectly, however, there must exist an additional site of action for the xanthines allowing them to interfere with the signal transduction pathway by a different, although still unknown mechanism. This can be deduced from the fact that under stimulation of the T-cell by the cytokine IL-2 which represents a cAMP-independent stimulation of the immune response via the IL-2 receptor (Smith K. A.: Science 240 (1988), 1169–1175), xanthines (but not CysA) are potent down-regulators of this activation. A representative example will be given in Table 3 of this application.

On account of the global circulation-promoting effect of POF, coupled with good tolerability, various examples of a comedication of this xanthine with other pharmaceuticals such as anticoagulants, cyto-statics, virustatics, antibiotics or antimycotics are already known. In addition, a pharmacodynamic interaction of POF with dexamethasone in vitro and with OKT3 has also been reported (Han J. et al.: J. Exp. Med. 172 (1990), 391–394; Weinberg J. B. et al.: Blood 79 (1992), 3337–3343 ; Zabel P. et al.: Z. Transplantationsmed. 3 (1991), 62–65; Alégre M. L. et al.: Transplantation 52 (1991), 674–679). As far as a combination with CysA is concerned, the general possibility that a comedication with immunosuppressives such as CysA can occur when using xanthines in immunological problems is already addressed in the patent applications EP 0 493 682 and EP 0 490 181. Although immunosuppressive properties are ascribed to the xanthines in these two patents, nevertheless no respective combination effect with other immunosuppressives has been derived therefrom. Independently, reports of a positive interaction of POF with CysA are known but relate exclusively to the tolerability problems (Brunner L. J. et al.: Renal Fail. 11 (1989), 97–104; Berkenboom G. et al.: J. Cardiovasc. Pharmacol. 18 (1991), 761–768; Rossi S. J. et al.: Drug Saf. 9 (1993), 104–131; WO 93/17684 caused by CysA medication, which presumably can be understood through inhibition of the formation of cytokines and endothelin (Carrier M. et al.: Ann. Thorac. Surg. 55 (1993), 490–492; Bennett W. M. et al.: Transplantation 54 (1992), 1118–1120) or an increase in renal prostaglandin synthesis (Brunnar L. J. at al. Renal Fail. 11 (1989), 97–104; Bennett W. M. et al.: Transplantation 54 (1992), 1118–1120, Bianco J. et al.: Blood 78 (1991), 1205–1211). Even when using POF in transplantation-related indications such as the GvH (graft-versus-host) reaction in which the treatment with CysA is part of the standard medication, the question is addressed exclusively to reduction of the toxicity of CysA (Bianco J. et al.: Blood 78 (1991), 1205–1211: Vogelsang G. B.: Curr. Opin. Oncol. 5 (1993), 276–281), although even this POF effect is not undisputed (Attal M. et al.: Blood 82 (1993), 732–736; van der Jagt R. H. C. et al.: Bone marrow Transplant. 13 (1994), 203–207).

FK506 (Tacrolimus) is a macrolide which exerts largely similar effects as CysA, both with regard to its molecular mode of action and its clinical efficacy (Liu J.: Immunol. Today 14 (1993), 290–295; Schreiber S. L. et al.: Immunol. Today 13 (1992), 136–142); respective effects, however, may be found already at doses which are less by the factor 20 to 100 compared to CysA (Peters D. H. et al.: Drugs 46 (1993), 746–794). The same is true for rapamycin (RPM) which again is a macrolide binding intracellularly to the same immunophilin as FK506, although the following biochemical events are differing somewhat (Morris R. E.: Transplant. Rev. 6 (1992), 39–87).

Various models of different estimations are available for testing an immunosuppressive action. In vivo, for example, different transplantation models are established presenting with different immunogenicities, depending on the donor and recipient species used and depending on the nature of the transplanted organ. The comparison of the length of the survival time of the transplanted organ in vivo with and without pharmacological intervention can thus be used as a quantitative measure for the suppression of the immune response. In vitro, there exist likewise various models of differing value. The best known are lymphocyte activation tests, in which the extent of the activation is measured via lymphocyte proliferation. Inhibition of proliferation thus always means immunosuppression under the experimental conditions applied. There exist different stimuli for lymphocyte activation:

coculture of lymphocytes of different species (MLR= mixed lymphocyte reaction): lymphocytes containing different antigens of the HLA-DR type (=allogens) activate each other non-specifically.

CD3 assay: specific activation of the T-lymphocytes via an exogenously added antibody (OKT3) against the CD3 marker molecule located on the lymphocyte membrane, together with a costimulatory signal. This activation proceeds via the $Ca^{2+}$/calmodulin/calcineurin system and can be inhibited by CysA CD28 assay: specific activation of the T-lymphocyte via an exogenously added antibody against the CD28 marker molecule located on the lymphocyte membrane, together with a costimulatory signal. This activation is $Ca^{2+}$-independent and thus cannot be inhibited by CysA.

IL-2R assay: specific activation of the lymphocyte via the exogenously added cytokine IL-2 which binds to the IL-2 receptor (IL-2R) located on the lymphocyte membrane. This activation is $Ca^{2+}$/cAMP-independent and cannot be inhibited by CysA.

It has now been found that the comedication of an immunosuppressive compound such as CysA or FK506 or RPM with a xanthine derivative leads to a superadditive increase in the immunosuppressive action. This becomes clear from Table 2 where each immunosuppressive, in combination with compound no. 1 (=xanthine derivative), demonstrates superadditive effect with regard to inhibition of proliferation in the MLR assay, as compared with the effect of the respective monosubstances. Under in vivo conditions in the rat heart allograft model this synergistic effect could indeed be confirmed, as treatment of the recipient animal with subtherapeutic doses of both compound no. 1 and CysA results in a significant prolongation of the survival time of the transplant (Table 4). As no interference with the respective drug levels could be found, this effect cannot be explained by changed pharmacokinetics, instead it is obviously a matter of increased pharmacodynamics.

Interestingly, xanthines are found to exert their actions by different mechanistic ways as compared to CysA, FK506, or RPM. Whereas compound no. 1 is active in all the applied in vitro tests regardless whether the stimulation of the immune response is dependent on specific intracellular levels of cAMP and/or $Ca^{2+}$ or not, CysA exerts its effect only in the MLR and the CD3 assays but not in the CD28 or IL-2R assays (Table 3). The same is true for FK506, whereas RPM is known to be effective in the IL-2R assay but, in contrast to the other immunosuppressives, not effective if IL-2 production itself is addressed (Morris R. E.: Rev. 6 (1992), 39–87). These data indicate that in combinations of xanthines with either CysA, FK506, or RPM, the resulting superadditive immunosuppressive effect may not only quantitatively be increased, but should also qualitatively be changed. This interpretation is supported by in vivo data demonstrating an indefinite survival of the transplant under special experimental conditions even after stop of the combination treatment, which may be explained by induction of immune tolerance (Table 5).

The therapeutic spectrum of action of the individual components is thus quantitatively and qualitatively broadened by a combination of this type. Moreover, it makes possible, by means of a dose reduction without reduced efficacy but with increased safety associated therewith, the treatment of even those immune disorders which were hitherto closed to immunosuppressive therapy as a result of intolerable incompatibility phenomena. At the same time, the therapy costs can be decreased to an appreciable extent. The invention therefore relates to a combination preparation, containing 1) cyclosporin A or FK506 or rapamycin,
2) at least one xanthine of the formula I,

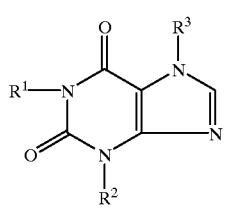
(I)

where $R^2$ is $(C_1-C_4)$-alkyl, and
one of the radicals $R^1$ or $R^3$ is a radical of the formula II

(II)

in which A
a) is a covalent single bond, where n is the integer 0, 1, 2, 3, 4, 5, 6 or 7, b) is a radical

where n is the integer 1, 2, 3, 4, 5 or 6, or
c) is a radical

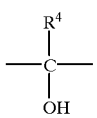

where n is the integer 1, 2, 3, 4, 5 or 6 and
$R^4$ is
  a) a hydrogen atom or
  b) $(C_1-C_3)$-alkyl,
and the other radical $R^1$ or $R^3$ is
  a) a hydrogen atom,
  b) $(C_1-C_7)$-alkyl,
  c) $(C_4-C_8)$-cycloalkyl-alkyl or
  d) alkyl having 1 to 6 carbon atoms, whose carbon chain is interrupted by an oxygen atom, and
3) a pharmaceutical excipient, for the simultaneous, separate or sequential use in organ transplantation, with the exception of the case in which cyclosporin A and 3,7-dimethyl-1-(5-oxohexyl)xanthine are employed for the treatment of bone marrow transplantations.

A xanthine of the formula I is preferred where $R^2$ is $(C_1-C_4)$-alkyl, one of the radicals $R^1$ or $R^3$ is a radical of the formula II, in which A is
  a) a radical

or
  b) a radical

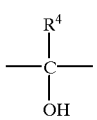

where n is the integer 3, 4, 5 or 6 and $R^4$ has the abovementioned meaning, and
the other radical $R^1$ or $R^3$ is $(C_1-C_7)$-alkyl or $(C_4-C_8)$ cycloalkyl-alkyl.

A xanthine of the formula I is especially preferred where $R^1$ and $R^3$ have the abovementioned meaning and $R^2$ is $(C_1-C_2)$-alkyl and $R^4$ is a hydrogen atom or $(C_1-C_2$-alkyl.

A xanthine of the formula I is particularly preferred where $R^2$ is $(C_1-C_2)$-alkyl,
$R^1$ is the radical of the formula II, in which A is a) a radical

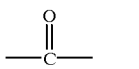 or b) a radical

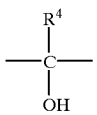

where n is the integer 3, 4, 5 or 6 and
R$^4$ is
a) a hydrogen atom or
b) (C$_1$–C$_2$)-alkyl, and
R$^3$ is (C$_1$–C$_7$)-alkyl or (C$_4$–C$_8$)-cycloalkyl-alkyl.

A xanthine of the formula I is very particularly preferred where
R$^2$ is (C$_1$–C$_2$)-alkyl,
R$^1$ is the radical of the formula II, in which A is
a) a radical

 or b) a radical

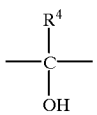

where n is the integer 3, 4, 5 or 6 and
R$^4$ is
a) a hydrogen atom or
b) (C$_1$–C$_2$)-alkyl, and
R$^3$ is (C$_2$–C$_5$)-alkyl or (C$_4$–C$_6$)-cycloalkyl-alkyl.

The compounds 1,3-dimethylxanthine, 3,7-dimethylxanthine, 1,3,7-trimethylxanthine, 1-hexyl-3,7-dimethylxanthine, 3,7-dimethyl-1-(5-oxohexyl)xanthine, 1-(5-hydroxyhexyl)-3,7-dimethylxanthine, 1,3-dimethyl-7-(5-oxohexyl)-xanthine, 7-(5-hydroxyhexyl)-1,3-dimethylxanthine, 1,3-di-n-butyl-7-(2-oxopropyl)xanthine, 1,3-di-n-butyl-7-(3-oxobutyl)-xanthine, 3-methyl-1-(5-oxohexyl)-7-propylxanthine, 1-(5-hydroxyhexyl)-3-methyl-7-propyl-xanthine, 1-(5-hydroxy-5-methylhexyl)-3-methyl-7-propylxanthine, 7-ethoxymethyl-1-(5-hydroxy-5-methylhexyl)-3-methylxanthine, 1-(5hydroxy-5-methylhexyl)-3-methylxanthine, 1-(5-hydroxy-5-methylhexyl)-3-methyl-7-butylxanthine, 1-(5-hydroxy-5-methylhexyl)-3,7-dimethylxanthine, 1-(6-hydroxy-6-methylheptyl)-3-methyl-7-propylxanthine, 3-ethyl-1-(5-hydroxy-5-methylhexyl)-7-propylxanthine, 3-ethyl-1-(6-hydroxy-6-methylheptyl)-7-propylxanthine, 7-butyl-3-ethyl-1-(6-hydroxy-6-methylheptyl)-xanthine or 7-cyclopropylmethyl-1-(5-hydroxy-5-methylhexyl)-3-methylxanthine are employed by way of example in the combination preparation according to the invention in combination with CysA or FK506 or rapamycin.

The term "(C$_4$–C$_8$)" is understood as an alkyl residue, which is substituted by a (C$_3$–C$_6$)-cycloalkyl and wherein the number of all carbon-atoms are from 4 to 8. Examples if these residues are cyclopropylmethyl, cyclopropylpentyl, cyclohexylmethyl or cyclohexylethyl. The term "(C$_4$–C$_6$)-cycloalkyl-alkyl" is understood as an alkyl residue, which is substituted by a (C$_3$–C$_5$)-cycloalkyl and wherein the number of all carbon-atoms are from 4 to 6.

The term "organ" is understood as meaning all organs or parts of organs (even several) in mammals, in particular humans, for example kidney, heart, skin, liver, muscle, cornea, bone, bone marrow, lung, pancreas, intestine or stomach.

In organ transplantation, rejection reactions of the organ recipient to the transplanted organ or rejection reactions of the transplanted organ to the recipient (host-versus-graft reaction or graft-versus-host reaction) occur. Rejection reactions mean all reactions of the recipient body or of the transplanted organ which in the end lead to cell or tissue death in the transplanted organ or adversely affect the functional ability and viability of the transplanted organ or the recipient. In particular, this means acute and chronic rejection reactions.

The term "superadditive actions" is understood as meaning effects which are greater than the sum of the actions of the individual components.

The xanthine derivatives are prepared by known processes (U.S. Pat. Nos. 3,737,433; 4,108,995; 4,833,146).

The invention also relates to novel trisubstituted xanthine derivatives of the formula I, in which
R$^3$ denotes butyl, and where
a) R$^1$ denotes 5-hydroxy-5-methylhexyl and R$^2$ denotes methyl, or
b) R$^1$ denotes 6-hydroxy-6-methylheptyl and R$^2$ denotes ethyl.

A further embodiment of the invention concerns novel xanthine compounds of the formula I,
where R$^2$ is (C$_1$–C$_4$)-alkyl, and
one of the radicals R$^1$ or R$^3$ is a radical of the formula II

in which A
a) is a covalent single bond, where n is the integer 0, 1, 2, 3, 4, 5, 6 or 7,
b) is a radical

where n is the integer 1, 2, 3, 4, 5 or 6, or
c) is a radical

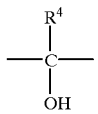

where n is the integer 1, 2, 3, 4, 5 or 6 and
R$^4$ is a hydrogen atom or (C$_1$–C$_3$)-alkyl,
and the other radical R$^1$ or R$^3$ is (C$_4$–C$_8$)-cycloalkyl-alkyl.

The invention further relates to compounds of the formula I,
where R$^2$ is (C$_1$–C$_4$)-alkyl,
one of the radicals R$^1$ or R$^5$ is a radical of the formula II, in which A is a) a radical

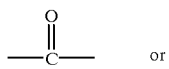 or b) a radical

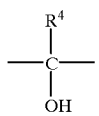

where n is the integer 3, 4, 5 or 6 and $R^4$ has the abovementioned meaning,
and the other radical $R^1$ or $R^3$ is $(C_4-C_8)$-cycloalkyl-alkyl.

The invention especially relates to compounds of the formula I, where
$R^2$ is $(C_1-C_2)$-alkyl,
$R^1$ is the radical of the formula II, in which A is
a) a radical

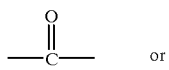 or b) a radical

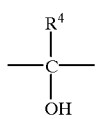

where n is the integer 3, 4, 5 or 6 and
$R^4$ is
a) a hydrogen atom or
b) $(C_1-C_2)$-alkyl, and
$R^3$ is $(C_4-C_8)$-cycloalkyl-alkyl.

The invention also relates to compounds of the formula I, where
$R^2$ is $(C_1-C_2)$-alkyl,
$R^1$ is the radical of the formula II, in which A is
a) a radical

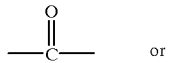 or b) a radical

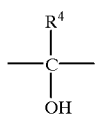

where n is the integer 3, 4, 5 or 6 and
$R^4$ is
a) a hydrogen atom or
b) $(C_1-C_2)$-alkyl, and
$R^3$ is $(C_4-C_6)$-cycloalkyl-alkyl.

The invention especially relates to the novel compound 7-cyclopropylmethyl-1-(5-hydroxy-5-methylhexyl)-3-methylxanthine.

The invention further relates to a combination preparation, containing 1) cyclosporin A or FK506 or rapamycin, 2) at least one xanthine of the formula I, and 3) a pharmaceutical excipient, for simultaneous, separate or sequential use in (auto)immune disorders.

These include, inter alia, systemic lupus erythematosus, rheumatoid arthritis, psoriasis, pemphigus, atopic dermatitis, myositis, multiple sclerosis, nephrotic syndrome (in particular glomerulonephritis), ulcerative colitis or juvenile diabetes.

The invention further relates to the use of cyclosporin A or FK506 or RPM and at least one xanthine of the formula I for the production of a pharmaceutical for inhibiting the replication of viruses such as picorna-, toga-, bunya-, orthomyxo-, paramyxo-, rhabdo-, retro-, arena-, hepatitis B-, hepatitis C-, hepatitis D-, adeno-, vaccinia-, papilloma-, herpes-, varicella-zoster-virus or human immunodeficiency virus (HIV); or for treating of cancer such as lung cancers, leukaemia, ovarian cancers, sarcoma, Kaposi's sarcoma, meningioma, colon cancers, lymph node tumors, glioblastoma multiforme, prostate cancers or skin carcinoses.

The invention further relates to the use of cyclosporin A or FK506 or rapamycin and at least one xanthine of the formula I for the production of a pharmaceutical for the treatment of humans after organ transplantation or of (auto) immune disorders.

The invention further relates to a combination preparation, containing 1) cyclosporin A or FK506 or rapamycin, and 2) at least one xanthine of the formula I, in a quantity producing a superadditive immunosuppressive effect.

The weight ratio of CysA (component 1) to the compound of the formula I is in general from 1:1 to 1:50, preferably from 1:2 to 1:25, in particular from 1:5 to 1:20. The weight ratios of FK506 or RPM (component 1) to the component 2 is in general from 1:50 to 1:2500, preferably from 1:100 to 1:1250, in particular from 1:250 to 1:1000.

The combination preparation according to the invention can be present as a dose unit in the form of pharmaceutical forms such as capsules (including microcapsules), tablets (including coated tablets and pills) or suppositories, when using capsules it being possible for the capsule material to take the function of the excipient and the contents to be present e.g. as a powder, gel, emulsion, dispersion or solution. It is particularly advantageous and simple, however, to prepare oral (peroral) formulations containing the two active compound components 1) and 2), which contain the calculated amounts of the active compounds together with any desired pharmaceutical excipient. An appropriate formulation (suppository) can also be used for rectal therapy. The transdermal, parenteral (intraperitoneal, intravasal, subcutaneous or intramuscular) or oral administration of solutions which contain the combinations according to the invention is possible as well.

The tablets, pills or granule bodies can be prepared by customary methods such as pressing, immersion or fluidized bed methods or pan coating and contain excipients and other customary auxiliaries, such as gelatine, agarose, starch, e.g. potato, corn or wheat starch, cellulose such as ethylcellulose, silica, various sugars such as lactose, magnesium carbonate and/or calcium phosphates. The coating solution usually comprises sugar and/or starch syrup and usually additionally contains gelatine, gum arabic, polyvinylpyrrolidone, synthetic cellulose esters, surface-active substances, plasticizers, pigments and similar additives according to the prior art. To prepare the pharmaceutical forms, any customary flow-regulating agent, lubricant or glidant such as magnesium stearate, and release agents can be used.

The preparations preferably have the form of coated/core tablets or multilayer tablets, the xanthine of the formula I being in the coating or in the core or in a layer, while cyclosporin A or FK506 or RPM is in the core or in the coating or in another layer. The active compound components can also be present in depot form or adsorbed on depot material or included in the depot material (e.g. those based on cellulose or polystyrene resin, e.g. hydroxyethylcellulose). Suitable xanthine components are also commercially available pharmaceutical preparations which are released with a time delay, e.g. only in the intestinal tract. A delayed release of the active compounds can also be aehieved by providing the layer or the compartment concerned with customary enteric coatings.

The dosage to be used is of course dependent on various factors such as the organism to be treated (e.g. human or animal, age, weight, general state of health), the severity of the symptoms, the disorder to be treated, possible accompanying disorders, (if present) the nature of the accompanying treatment with other pharmaceuticals, or the frequency of the treatment. The dosages are in general administered several times per day and preferably once to three times per day. The amounts of the individual active compounds should be within the range given below, e.g. within the tolerable, efficacious dosage range for the organism to be treated.

Suitable therapy with the combinations according to the invention thus comprises e.g. the administration of one, two or 3 to 8 individual dosages of the combination preparations according to the invention of 1) 25 mg to 100 mg each, preferably from 10 to 20 mg of cyclosporin A, and 2)100 to 1200 mg, preferably 400 to 600 mg, of xanthine of the formula I, the amount naturally being dependent on the number of individual dosages and on the disorder to be treated and it also being possible for an individual dose to comprise several dose units administered simultaneously. The dose in the case of oral administration is in general at most 5 to 10 mg/kg/day of CysA (component 1), where a serum level of 100 ng/ml to 200 ng/ml should not be exceeded, and at most 20 mg/kg/day of a compound of the formula I, in particular in the case of oral or rectal administration. In the case of i.v. or i.p. administration, the upper daily dose of these active compounds in general is by 40% to 50% lower.

If FK506 or RPM is employed instead of CysA the dosage is distinctly lower. In the case of oral administration, in general from 0.02 to 0.2 mg/kg/day, preferably 0.035 to 0.1 mg/kg/day, in particular 0.04 to 0.08 mg/kg/day, of FK506 or RPM is employed as component 1.

The combination preparation according to the invention can also include combination packs or compositions in which the constituents are placed side by side and can therefore be administered simultaneously, separately or sequentially to one and the same human or animal body.

EXAMPLE 1

Mixed Human Lymphocyte Reaction (MLR) Assay

Human peripheral blood mononuclear cells (PBMC) are gained from healthy volunteers by density gradient centrifugation through Ficoll-Hypaque (Pharmacia, Uppsala), washed in Hank's solution (HBSS) and resuspended in culture medium (RPMI-1640+10% fetal calf serum+1% penicillin/streptomycin, Biochrom, Berlin) to give a cell count of $1 \times 10^6$ cells/ml. 100 $\mu l$ of those PBMC are mixed with 100 $\mu l$ of irradiated PMBC ($1 \times 10^6$ cells/ml) in a well of a microtiter plate. The test substances, alone or in combination, are likewise added to the PBMC. The plates are incubated for 5 days at 37° C. in a moist atmosphere which contains 5% $CO_2$. Then 1 $\mu Ci$ of $^3H$-thymidine is added to the cells and they are incubated under the above-mentioned conditions for a further 8 hours. The cells are then collected on glass fiber filters and the incorporated radioactivity is determined using a beta counter.

Table 1 shows the effect of different xanthine derivatives under comparable conditions (all 100 $\mu M$) on lymphocyte proliferation in the MLR assay. Inhibition is given in percent and referred to uninhibited controls (which correspond to 0%).

Table 2 shows a superadditive action on lymphocyte proliferation in the MLR assay when compound no. 1 is administered in combination with CysA, FK506, or RPM, respectively. Inhibition is given in percent and referred to uninhibited controls (which correspond to 0%)

TABLE 1

| Compound of the formula I | $R^1$ | $R^2$ | $R^3$ | % inhibition of proliferation (100 $\mu M$) |
|---|---|---|---|---|
| 1 | $CH_3-C(CH_3)(OH)-(CH_2)_4$ | $CH_3$ | $C_3H_7$ | 69 |
| 2 | $C_3H_7$ | $CH_3$ | $CH_3-C(CH_3)(OH)-(CH_2)_4$ | 77 |
| 3 | $CH_3-CH(OH)-(CH_2)_4$ | $CH_3$ | $C_3H_7$ | 83 |
| 4 | $CH_3-C(C_2H_5)(OH)-(CH_2)_4$ | $CH_3$ | $C_3H_7$ | 72 |
| 5 | $CH_3-C(CH_3)(OH)-(CH_2)_3$ | $CH_3$ | $C_3H_7$ | 45 |

TABLE 1-continued

| Compound of the formula I | R$^1$ | R$^2$ | R$^3$ | % inhibition of proliferation (100 μM) |
|---|---|---|---|---|
| 6 | CH$_3$—C(CH$_3$)(OH)—(CH$_2$)$_5$ | CH$_3$ | C$_3$H$_7$ | 87 |
| 7 | CH$_3$—C(CH$_3$)(OH)—(CH$_2$)$_4$ | C$_2$H$_5$ | C$_3$H$_7$ | 86 |
| 8 | CH$_3$—C(CH$_3$)(OH)—(CH$_2$)$_4$ | CH$_3$ | C$_4$H$_9$ | 91 |
| 9 | CH$_3$—C(CH$_3$)(OH)—(CH$_2$)$_4$ | CH$_3$ | H$_3$C—CH$_2$—O—CH$_2$ | 61 |
| 10 | CH$_3$—C(CH$_3$)(OH)—(CH$_2$)$_5$ | C$_2$H$_5$ | C$_3$H$_7$ | 90 |
| 11 | CH$_3$—C(CH$_3$)(OH)—(CH$_2$)$_5$ | C$_2$H$_5$ | C$_4$H$_9$ | 94 |
| 12 | CH$_3$—C(CH$_3$)(OH)—(CH$_2$)$_4$ | CH$_3$ | 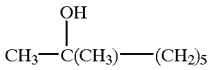 | 85 |
| 13 | CH$_3$—C(CH$_3$)(OH)—(CH$_2$)$_4$ | CH$_3$ | CH$_3$ | 66 |
| 14 | CH$_3$—(CH$_2$)$_5$ | CH$_3$ | CH$_3$ | 85 |

TABLE 2

| Treatment with immunosuppressant | CysA 20 nM | FK 506 0.5 nM | RPM 0.5 nM |
|---|---|---|---|
| alone | 10% | 30% | 35% |
| in combination with compound no. 1 (10 μM)* | 30% | 55% | 65% |

*compound no. 1 alone (10 μM) inhibits lymphocyte proliferation under the conditions applied by <5%

EXAMPLE 2

CD3 and CD28 Assays
A) Isolation of T-lymphocytes

T-lymphocytes are purified from PBMC. Lympho-KWIK-T (One Lambda Inc., Los Angeles, Calif., USA), a mixture of monoclonal antibodies from anti-monocytes and anti-B cells and complement, together with a mixture of monoclonal anti-NK and anti-monocyte antibodies with Leu 11b (anti-CD16, IgM) and Leu 7 (anti-CD57, IgM), is employed for purification. Purification relates to the following process steps:

PMBC are islated from peripheral blood in a density gradient.

Monocytes are removed by cold agglutination.

30×10$^6$ cells obtained are incubated with 0.8 ml of Lympho-KWIK-T for 1 hour at 37° C.

The cells are washed three times and then incubated for 30 minutes at 4° C. with the monoclonal anti-NK and anti-monocyte antibody mixture.

The cells are washed once and incubated again with 0.8 ml of Lympho-KWIK-T for 1 hour at 37° C.

The cells are washed three times and resuspended in a culture medium.

The cell preparation contains more than 97% of T-lymphocytes (D3+). This is determined by flow cytometry.
B) Test Procedure 5×10$^4$ T-lymphocytes are incubated in 200 μl of culture medium (RPMI 1640; Gibco, Life Technologies GmbH, Germany, mixed with 10% fetal bovine serum, penicillin and streptomycin) in microtiter plates having a flat bottom, containing monoclonal OKT3 or anti-CD28 antibodies (in each case 1 μg/ml of each of the monoclonal antibodies) and phorbol myristate acetate (PMA; Sigma Chemie, Switzerland; 5 ng/ml). 4 identical batches in each case are cultured at 37° C. in a 5% CO$_2$ atmosphere. The test substances are added to the cells at the final concentrations given. After 64 hours, 1 μCi of $^3$H-thymidine in each case is added to the cells. 8 hours later the cells are collected on glass fiber filters and the incorporated radioactivity is measured as in Example 1.

The percentage inhibition of the T-lymphocyte proliferation by the test substances is based on a control without test substances taking into account a basal value without the immunological stimulus. For results see Table 3 (under Example 3).

EXAMPLE 3

IL-2R Assay

The murine lymphocytic cell line CTLL-2 (ATCC, Rockville/USA), is washed and resuspended in culture medium to give a cell count of $8 \times 10^4$ cells/ml. 50 µl corresponding to $4 \times 10^3$ cells are mixed with 30 µl of mouse recombinant IL-2 (final concentration 0.35 ng/ml) and 20 µl of the test substances at different concentrations or vehicle in a micro-titer plate well. After 48 h incubation at 37° C. in a $CO_2$ incubator 10 µl of WST-1 reagent (Boehringer Mannheim) is added, and after a further 4-h incubation at 37° C. the optical density of the sample is measured at 450 nm vs. 630 nm (Behring EL-31 spectrophotometer). Cleavage of the tetrazolium salt WST-1 by mitochondrial hydrogenases correlates with the number of viable cells and, therefore, with the extent of proliferation. Data are given as % inhibition, based on uninhibited controls and taking into account a basal value without the IL-2 stimulus.

Table 3 summarizes the effects of CysA and compound no. 1, respectively, in all the applied in vitro test systems. Respective data are obtained according to Examples 1 (MLR assay), 2 (CD3 and CD28 assays) and 3 (IL-2R assay).

|  | MLR assay | CD3 assay | CD28 assay | IL-2R assay |
|---|---|---|---|---|
|  | % inhibition of proliferation | | | |
| CysA 40 nM | 40 | 50 | 10 | <5 |
| compound no. 1 40 µM | 35 | 40 | 55 | 45 |

EXAMPLE 4

Transplantation Model

The hearts of WAKH rats (body weight 150–200 g) are implanted heterotopically into the peritoneal cavity of male PVG rats (body weight 200–250 g). The transplantation is carried out under anesthesia. Functional control of the transplanted heart by palpation is carried out daily, and rejection is defined by stop of beating. The administration of the test substances is carried out individually or in combination once daily via stomach tube. Alternatively, the xanthine derivative is administered parenterally by means of an osmotic minipump, which allows a continuous intravenous administration of the daily dose over 24 h.

TABLE 4

Survival time of heterotopic heart transplants in the allogeneic rat model (WKAH[donor] → PVG[decipient]); all drugs have been given orally once daily by gavage.

| Kind of treatment | Dosage (mg/kg/day) p.o. | Treatment period (days) | Number (n) | Survival time (days) |
|---|---|---|---|---|
| (Control) | — | — | 5 | 4, 5, 5, 5, 7 |
| CysA | 7.5 | −1 until rejection | 8 | 4, 4, 4, 4, 6, 6, 8, 9 |
| Compound no. 1 | 100 | −1 until rejection | 2 | 4, 6 |
| CysA + compound no. 1 | 7.5 +} 100 } | −1 to 30 | 8 | >14*, >20*, 36, 38, 39, 40, 41, 42 |

*Death of the animal, with still beating transplanted heart, after puncture of its original heart for purpose of blood withdrawal

TABLE 5

Survival time of heterotopic heart transplants in the allogeneic rat model (WKAH[donor]→PVG[recipient]); the xanthine derivative has been given intravenously by osmotic minipump.

| Kind of treatment | Dosage (mg/kg/day) | Treatment period (days) | Number (n) | Survival time (days) |
|---|---|---|---|---|
| (Control) | — | — | 5 | 4, 5, 5, 5, 7 |
| CysA | 7.5 p.o. | −1 until rejection | 8 | 4, 4, 4, 4, 6, 6, 8, 9 |
| Compound no. 1 | 20 i.v. | −1 to 14 | 5 | 5*, 6*, 8*, 12, 14 |
| CysA + compound no. 1 | 7.5 p.o. 20 i.v. | −1 to 30 −1 to 14 | 3 | >50, >70, >160 |

*Clots in the pump disturbing/stopping drug administration

EXAMPLE 5

7-butyl-3-ethyl-1-(6-hydroxy-6-methylheptyl)-xanthine (comp. no. 11)

4.7 g of 7-butyl-3-ethylxanthine, 2.8 g of potassium carbonate, and 4.4 g of 1-bromo-6-hydroxy-6-methylheptane are stirred in 100 ml of dimethylformamide at 120° C. for 7 hours. The mixture is filtered hot with suction, the filtrate is concentrated under reduced pressure, the residue is taken up in chloroform, washed first with 2 N sodium hydroxide solution and then with water until neutral and dried over sodium sulphate, the solvent is distilled off under reduced pressure whereupon an oily crude product in virtually quantitative yield is obtained which can advantageously be purified by filtration over a silica gel column using a chloroform/methanol (10:1) mixture as mobile phase, followed by a final recrystallization from diisopropylether with addition of petroleum ether.

$C_{19}H_{32}N_4O_3$ (molecular weight=364.5); Melting point: 75–77° C.

In an analogous manner to Example 5 the following compounds were obtained.

EXAMPLE 6

1-(5-hydroxy-5-methylhexyl)-3-methyl-7-butylxanthine (comp. no. 8)

The title compound was prepared by using 7-butyl-3-methylxanthine and 1-chloro-5-hydroxy-5-methylhexane as starting materials. $C_{17}H_{28}N_4O_3$ (molecular weight=336.4); the oily product was characterized and identified by NMR mass-spectroscopy.

EXAMPLE 7

7-cyclopropylmethyl-1-(5-hydroxy-5-methylhexyl)-3-methylxanthine (compound no. 12)

The title compound was prepared by using 7-cyclopropylmethyl-3-methylxanthine and 1-chloro-5-hydroxy-5-methylhexane as starting materials.

$C_{17}H_{26}N_4O_3$ (molecular weight=334.4); Melting point: 92–94° C.

What is claimed is:

1. A method of suppressing the immune system in a subject in need thereof, comprising administering to the subject a superadditive immunosuppressive effective amount of:

(1) cyclosporin A or FK506 or rapamycin,
(2) at least one xanthine of the formula I

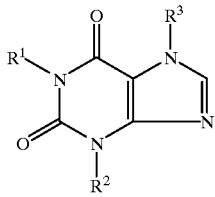 (I)

where $R^2$ is $(C_1-C_4)$-alkyl,
one of the radicals $R^1$ or $R^3$ is a radical of the formula II —$(CH_2)_n$—A—$CH_3$ (II)

in which A is selected from the group consisting of:
a radical

where n is the integer 1, 2, 3, 4, 5 or 6, and
a radical

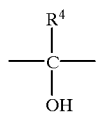

where n is the integer 1, 2, 3, 4, 5 or 6 and $R^4$ is a hydrogen atom or $(C_1-C_3)$-alkyl, and
the other radical $R^1$ or $R^3$ is selected from the group consisting of:
a hydrogen atom,
$(C_1-C_7)$-alkyl,
$(C_4-C_8)$-cycloalkyl-alkyl and
alkyl having 1 to 6 carbon atoms, whose carbon chain is interrupted by an oxygen atom, and
(3) a pharmaceutical excipient.

2. The method of claim 1, wherein the xanthine is a compound of the formula I in which
$R^2$ is $(C_1-C_4)$-alkyl,
one of the radicals $R^1$ or $R^3$ is a radical of the formula II, in which A is selected from the group consisting of:
a radical

where n is the integer 1, 2, 3, 4, 5 or 6, and
a radical

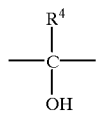

where n is the integer 1, 2, 3, 4, 5 or 6 and $R^4$ is a hydrogen atom or $(C_1-C_3)$-alkyl, and the other radical $R^1$ or $R^3$ is $(C_1-C_7)$-alkyl or $(C4-C8)$-cycloalkyl-alkyl.

3. The method of claim 2, wherein $R^2$ is $(C_1-C_2)$-alkyl and $R^4$ is a hydrogen atom or $(C_1-C_2)$-alkyl.

4. The method of claim 1, wherein the xanthine is a compound of the formula I in which
$R^2$ is $(C_1-C_2)$-alkyl,
$R^1$ is a radical of the formula II, in which A is selected from the group consisting of:
a radical

where n is the integer 1, 2, 3, 4, 5 or 6, and
a radical

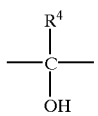

where n is the integer 1, 2, 3, 4, 5 or 6 and $R^4$ is a hydrogen atom or $(C_1-C_3)$-alkyl, and
$R^3$ is $(C_1-C_7)$-alkyl or $(C_4-C_8)$-cycloalkyl-alkyl.

5. The method of claim 1, wherein $R^3$ is $(C_2-C_5)$-alkyl or $(C4-C6)$-cycloalkyl-alkyl.

6. The method of claim 1, wherein the xanthine is selected from the group consisting of:

1-hexyl-3,7-dimethylxanthine,
1-(5-hydroxyhexyl)-3-methyl-7-propylxanthine,
1-(5-hydroxy-5-metylhexyl)-3-methyl-7-propylxanthine,
7-butyl-1-(5-hydroxy-5-methylhexyl)-3-methylxanthine,
1-(5-hydroxy-5-methylhexyl)-3,7-dimethylxanthine,
1-(6-hydroxy-6-methylheptyl)-3-methyl-7-propylxanthine,
3-ethyl-1-(5-hydroxy-5-methylhexyl)-7-propylxanthine,
3-ethyl-1-(6-hydroxy-6methylheptyl)-7-propylxanthine,
7-butyl-3-ethyl-1-(6-hydroxy-6-methylheptyl)-xanthine and
7-cyclopropylmethyl-1-(5-hydroxy-5-methylhexyl)-3-methylxanthine.

7. The method of claim 1, wherein the subject has a disorder selected from the group consisting of systemic lupus erythematosus, rheumatoid arthritis, psoriasis, pemphigus, atopic dermatitis, myositis, multiple sclerosis, nephrotic syndrome, glomerulonephritis, ulcerative colitis and juvenile diabetes.

8. The method of claim 1, wherein the subject is an organ transplant recipient.

9. The method of claim 1, wherein the subject has an immune system disorder.

10. The method of claim 1, wherein the subject is infected with a virus selected from the group consisting of picornavirus, togavirus, bunyavirus orthomyxoviris, paramyxovirus, rhabdovirus, retrovirus, arenavirus, hepatitis B, hepatitis C, hepatitis D, adenovirus, vaccinia virus, papilloma virus, herpes virus, varicella-zoster virus and human immune deficiency virus.

11. The method of claim 1, wherein the subject is suffering from a cancer selected from the group consisting of lung cancer, leukemia, ovarian cancer, sarcoma, Kaposi's sarcoma, meningioma, colon cancer, lymph node tumor, glioblastoma multiforme, prostrate cancer and skin carcinoses.

12. The method of claim 1, wherein the administering of (1), (2) and (3) is simultaneous.

13. A pharmaceutical composition comprising:
(1) cyclosporin A or FK506 or rapamycin,
(2) at least one xanthine of the formula I

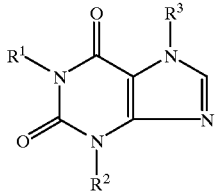
(I)

where $R^2$ is $(C_1-C_4)$-alkyl,
one of the radicals $R^1$ or $R^3$ is a radical of the formula II $$—(CH_2)_n—A—CH_3 \quad (II)$$

in which A is selected from the group consisting of:
  a radical

where n is the integer 1, 2, 3, 4, 5 or 6, and
  a radical

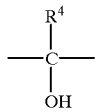

where n is the integer 1, 2, 3, 4, 5 or 6 and $R^4$ is a hydrogen atom or $(C_1-C_3)$-alkyl, and
the other radical $R^1$ or $R^3$ is selected from the group consisting of:
  a hydrogen atom,
  $(C_1-C_7)$-alkyl,
  $(C_4-C_8)$-cycloalkyl-alkyl and
  alkyl having 1 to 6 carbon atoms, whose carbon chain is interrupted by an oxygen atom, and
(3) a pharmaceutical excipient,
wherein said composition comprises a superadditive immunosuppressive effective amount of said xanthine of the formula I and said cyclosporin A or FK506 or rapamycin.

14. The composition of claim 13, wherein the xanthine is a compound of the formula I in which $R^2$ is $(C_1-C_4)$-alkyl,
one of the radicals $R^1$ or $R^3$ is a radical of the formula II, in which A is selected from the group consisting of:
  a radical

where n is the integer 1, 2, 3, 4, 5 or 6, and
  a radical

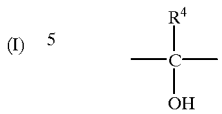

where n is the integer 1, 2, 3, 4, 5 or 6 and $R^4$ is a hydrogen atom or $(C_1-C_3)$-alkyl, and
the other radical $R^1$ or $R^3$ is $(C_1-C_7)$-alkyl or $(C_4-C_8)$-cycloalkyl-alkyl.

15. The composition of claim 14, wherein $R^2$ is $(C_1-C_2)$-alkyl and $R^4$ is a hydrogen atom or $(C_1-C_2)$-alkyl.

16. The composition of claim 13, wherein the xanthine is a compound of the formula I in which
  $R^2$ is $(C_1-C_2)$-alkyl,
  $R^1$ is the radical of the formula II, in which A is selected from the group consisting of:
    a radical

where n is the integer 1, 2, 3, 4, 5 or 6, and
  a radical

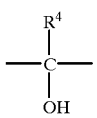

where n in the integer 1, 2, 3, 4, 5 or 6 and $R^4$ is a hydrogen atom or $(C_1-C_3)$-alkyl, and
  $R^3$ is $(C_1-C_7)$-alkyl or $(C_4-C_8)$-cycloalkyl-alkyl.

17. The composition of claim 16, wherein $R^3$ is $(C_2-C_5)$-alkyl or $(C_4-C_6)$-cycloalkyl-alkyl.

18. The composition of claim 13, wherein the xanthine is selected from the group consisting of:

1-hexyl-3,7-dimethylxanthine,
1-(5-hydroxyhexyl)-3-methyl-7-propylxanthine,
1-(5-hydroxy-5-methylhexyl)-3-methyl-7-propylxanthine,
7-butyl-1-(5-hydroxy-5-methylhexyl)-3-methylxanthine,
1-(5-hydroxy-5-methylhexyl)-3,7-dimethylxanthine,
1-(6-hydroxy-6-methylheptyl)-3-methyl-7-propylxanthine,
3-ethyl-1-(5-hydroxy-5-methylhexyl)-7-propylxanthine,
3-ethyl-1-(6-hydroxy-6-methylheptyl)-7-propylxanthine,
7-butyl-3-ethyl-1-(6-hydroxy-6-methylheptyl)-xanthine and
7-cyclopropylmethyl-1-(5-hydroxy-5-methylhexyl)-3-methylxanthine.

19. The composition of claim 13, in an amount effective to produce a superadditive immunosuppressive effect.

20. The method of claim 1, wherein the xanthine is administered at concentrations that are sub-therapeutic when administered in the absence of cyclosporin A or FK506 or rapamycin.

21. The composition of claim 13, wherein the xanthine is present in an amount that is sub-therapeutic in the absence of cyclosporin A or FK506 or rapamycin.

* * * * *